US009449148B2

(12) United States Patent
Holmes

(10) Patent No.: US 9,449,148 B2
(45) Date of Patent: Sep. 20, 2016

(54) SYSTEM AND METHOD FOR FILLING AND DISPENSING ORDERS

(71) Applicant: RxSafe, LLC, San Diego, CA (US)

(72) Inventor: William K. Holmes, San Diego, CA (US)

(73) Assignee: RxSafe, LLC, Vista, CA (US)

( * ) Notice: Subject to any disclaimer, the term of this patent is extended or adjusted under 35 U.S.C. 154(b) by 0 days.

(21) Appl. No.: 13/804,818

(22) Filed: Mar. 14, 2013

(65) Prior Publication Data

US 2014/0094958 A1    Apr. 3, 2014

Related U.S. Application Data

(60) Provisional application No. 61/708,935, filed on Oct. 2, 2012.

(51) Int. Cl.
*G06F 7/00* (2006.01)
*G06F 19/00* (2011.01)
*G07F 17/00* (2006.01)

(52) U.S. Cl.
CPC ....... *G06F 19/3456* (2013.01); *G06F 19/3462* (2013.01); *G07F 17/0092* (2013.01)

(58) Field of Classification Search
USPC ......................................................... 700/216
See application file for complete search history.

(56) References Cited

U.S. PATENT DOCUMENTS

| | | | |
|---|---|---|---|
| 4,267,942 A | 5/1981 | Wick, Jr. et al. | |
| 5,901,876 A | 5/1999 | Yuyama et al. | |
| 5,905,653 A * | 5/1999 | Higham et al. | ............... 700/244 |
| 6,048,086 A * | 4/2000 | Valerino, Sr. | ....... B01F 11/0005 514/474 |
| 6,711,460 B1 * | 3/2004 | Reese | ................. G06F 19/3456 700/216 |
| 6,883,681 B1 | 4/2005 | Coughlin et al. | |
| 7,672,859 B1 * | 3/2010 | Louie | .................... G06F 19/328 235/462.46 |
| 2001/0027634 A1 | 10/2001 | Hebron et al. | |
| 2004/0004085 A1 | 1/2004 | Williams | |
| 2004/0034447 A1 | 2/2004 | Vollm | |
| 2004/0059463 A1 | 3/2004 | Coughlin | |
| 2004/0093116 A1 * | 5/2004 | Mountz | ......................... 700/216 |
| 2005/0192705 A1 | 9/2005 | Pinney et al. | |
| 2006/0106488 A1 * | 5/2006 | Zito, Jr. | ....................... 700/231 |
| 2006/0161296 A1 | 7/2006 | Shoenfeld | |
| 2006/0277269 A1 | 12/2006 | Dent et al. | |
| 2007/0043469 A1 * | 2/2007 | Draper | ................ G06F 19/3462 700/231 |
| 2008/0247858 A1 | 10/2008 | Lourman et al. | |
| 2010/0030667 A1 * | 2/2010 | Chudy | ................ G06F 19/3462 705/28 |
| 2011/0046778 A1 * | 2/2011 | Pinney et al. | ................ 700/236 |
| 2011/0054668 A1 * | 3/2011 | Holmes | ............ G06Q 20/40145 700/216 |
| 2011/0184751 A1 | 7/2011 | Holmes | |
| 2012/0073241 A1 | 3/2012 | Mahar | |
| 2012/0118910 A1 | 5/2012 | Pinney et al. | |

OTHER PUBLICATIONS

International Search Report and Written Opinion for Application No. PCT/US2013/62866 dated Jun. 5, 2014 (22 pages).
Extended European Search Report from the European Patent Office for Application No. 13844463.3 dated May 30, 2016 (7 pages).

* cited by examiner

*Primary Examiner* — Kyle Logan
(74) *Attorney, Agent, or Firm* — Michael Best & Friedrich LLP

(57) ABSTRACT

A method of filling prescription orders includes inputting the prescription orders into a pharmaceutical storage and retrieval device, processing the prescription orders with the pharmaceutical storage and retrieval device to fill a plurality of vials with desired pharmaceuticals, and transferring the plurality of filled vials from the pharmaceutical storage and retrieval device to a storage unit. The method also includes storing the plurality of filled vials in the storage unit until a customer claims one of the plurality of filled vials and directing the one of the plurality of filled vials from the storage unit to the customer.

15 Claims, 3 Drawing Sheets

SYSTEM AND METHOD FOR FILLING AND DISPENSING ORDERS

CROSS-REFERENCE TO RELATED APPLICATIONS

This application claims priority to U.S. Provisional Patent Application No. 61/708,935, filed Oct. 2, 2012, the entire contents of which are incorporated by reference herein.

FIELD OF THE INVENTION

The present invention relates to systems and methods for filling and dispensing orders. More particularly, the present invention relates to systems and methods for filling and dispensing prescription orders to customers in retail pharmacy settings.

SUMMARY

In one embodiment, the invention provides a method of filling prescription orders. The method includes inputting the prescription orders into a pharmaceutical storage and retrieval device, processing the prescription orders with the pharmaceutical storage and retrieval device to fill a plurality of vials with desired pharmaceuticals, and transferring the plurality of filled vials from the pharmaceutical storage and retrieval device to a storage unit. The method also includes storing the plurality of filled vials in the storage unit until a customer claims one of the plurality of filled vials and directing the one of the plurality of filled vials from the storage unit to the customer.

In another embodiment, the invention provides a method of restocking unclaimed prescription orders. The method includes filling a vial with pharmaceuticals using a pharmaceutical storage and retrieval device, transferring the filled vial from the pharmaceutical storage and retrieval device to a storage unit, and storing the filled vial in the storage unit until a customer claims the filled vial. The method also includes monitoring a length of time that the filled vial is stored in the storage unit and returning the filled vial to the pharmaceutical storage and retrieval device if the filled vial is unclaimed by the customer after a predetermined period of time.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
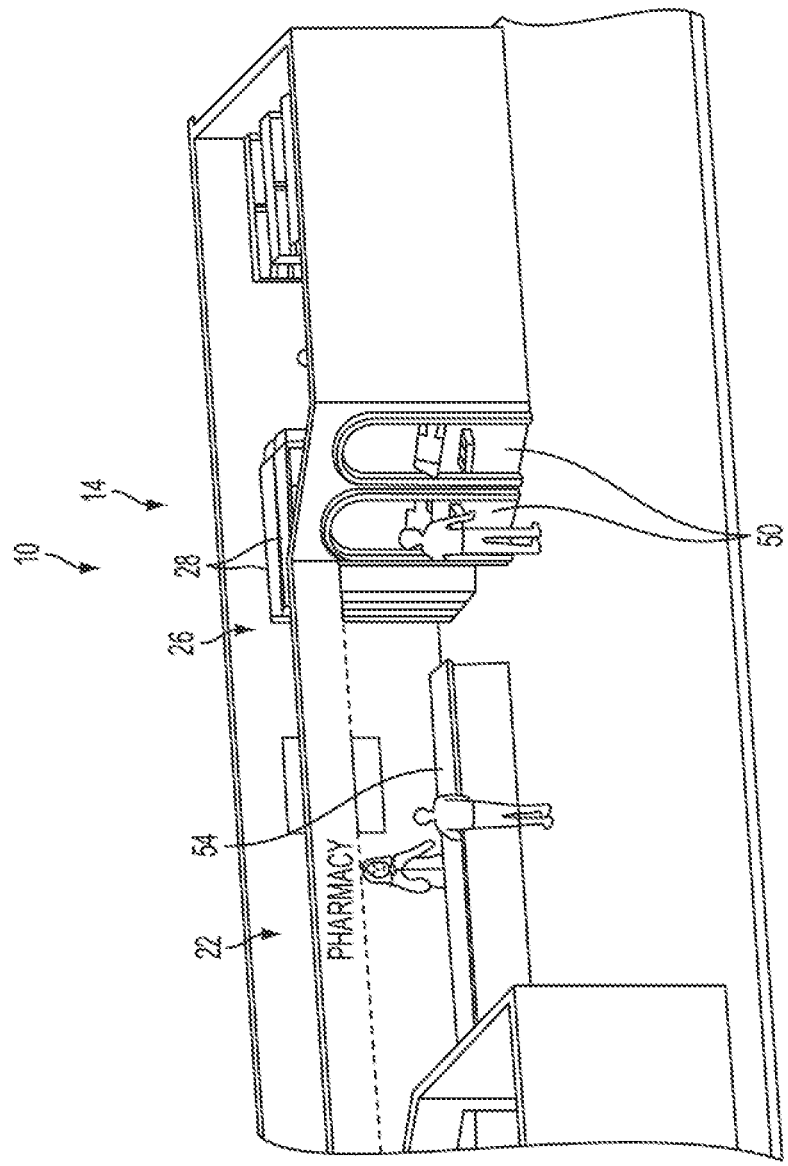
FIG. 1 is a front perspective view of a pharmacy including a system for filling and dispensing orders that embodies the invention.
Figure 2:
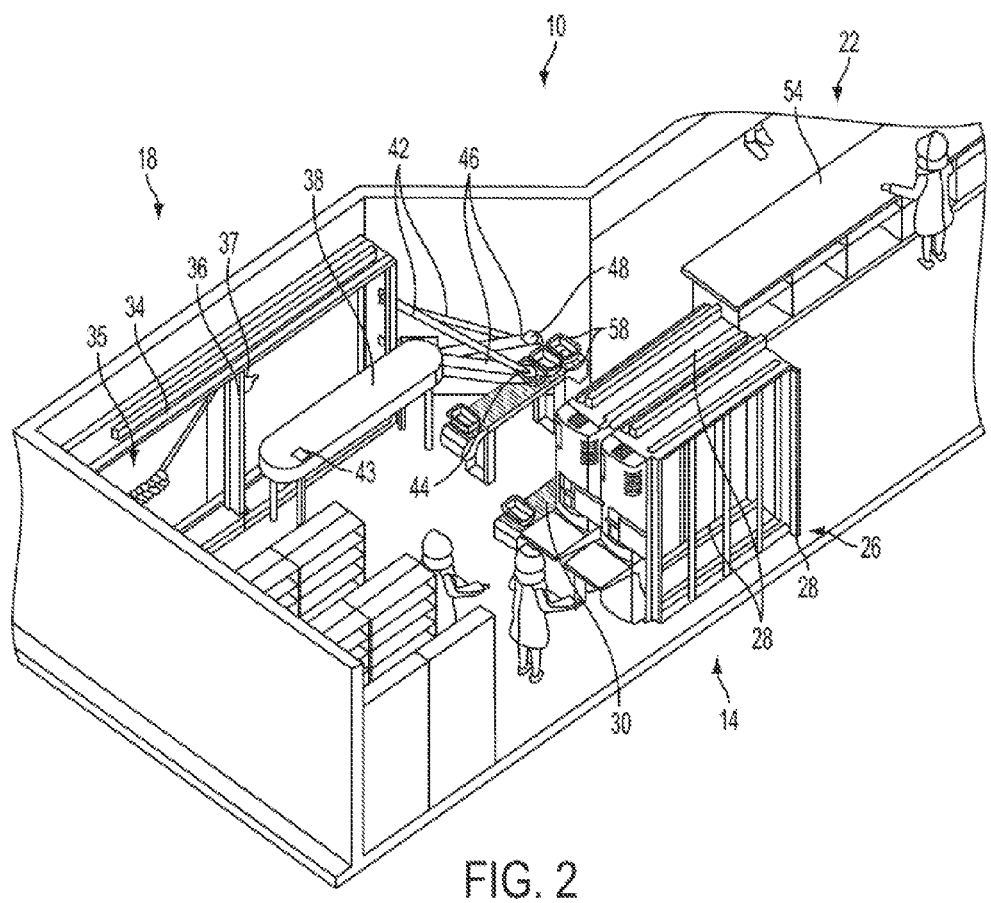
FIG. 2 is a rear perspective view of the pharmacy including the system for filling and dispensing orders.
Figure 3:
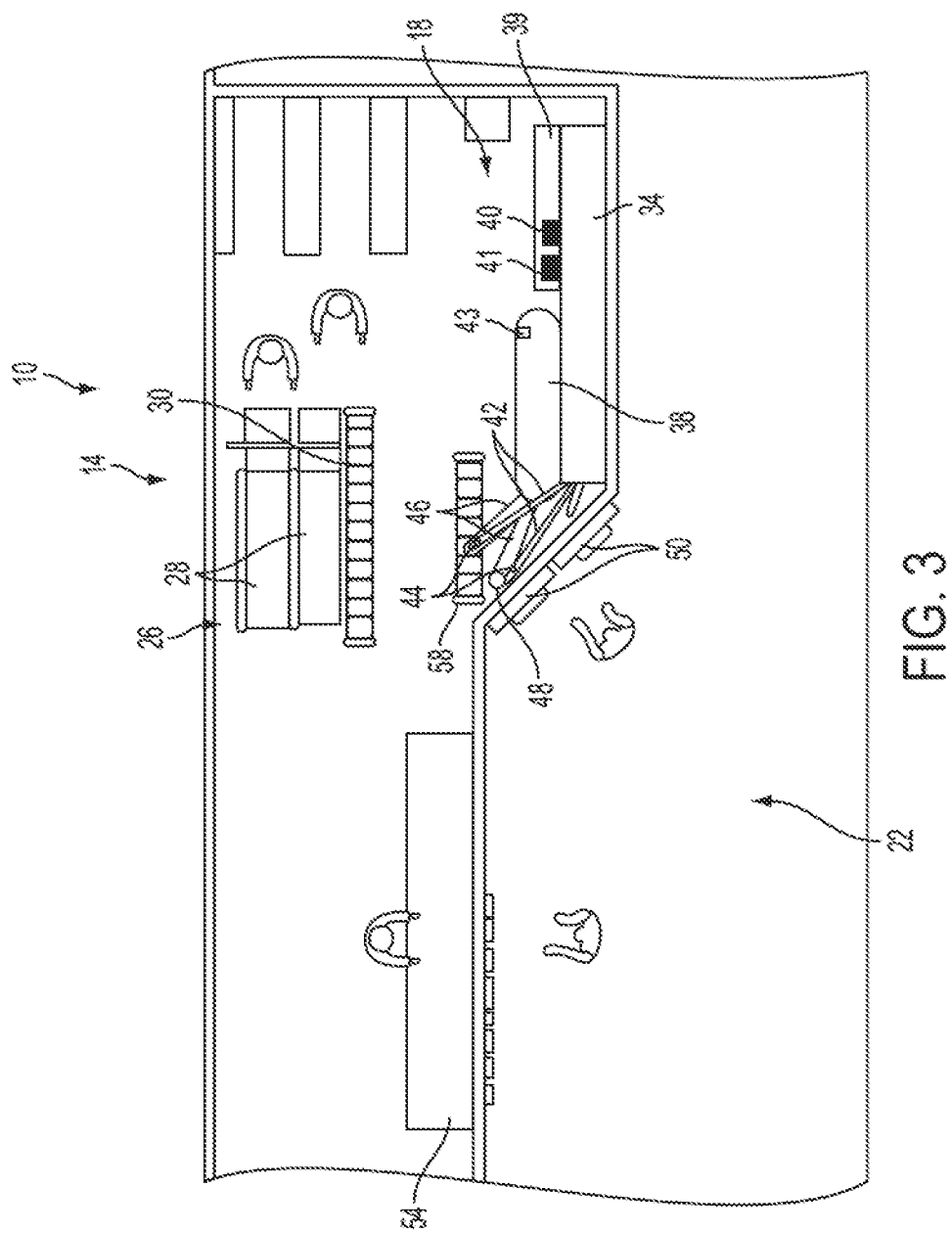
FIG. 3 is a top plan view of the pharmacy including the system for filling and dispensing orders.

FIGS. 1-3 illustrate a system 10 for filling and dispensing prescription drug or other pharmaceutical orders in a pharmacy. The illustrated system 10 includes a production area 14 for filling prescription orders, a will call area 18 for temporarily storing the filled prescriptions, and a sales area 22 for distributing the filled prescriptions to customers.

The production area 14, or room, is somewhat isolated and out of view of customers to create a more productive factory-like environment for processing and filling orders. The production area 14 may alternatively be visible to customers or managers within the pharmacy. The production area 14 includes a system 26 to fill prescription orders. In the illustrated embodiment, the system 26 includes two pharmaceutical storage and retrieval devices 28. The illustrated devices 28, or towers, are the pharmaceutical storage and retrieval devices disclosed in U.S. patent application Ser. No. 12/870,045, filed Aug. 27, 2010, the entire contents of which are incorporated by reference herein. In other embodiments, the system 26 can include fewer or more pharmaceutical storage and retrieval devices 28, depending on the volume or demand of prescription orders in the pharmacy.

The devices 28 receive and process prescription orders to fill vials and "unit of use" packs with the desired pharmaceuticals (e.g., drugs, narcotics, equipment, etc.). A control system including a processor, memory, and an input device is coupled to the devices 28. The input device allows a user (e.g., a pharmacist or other technician) to input a series of prescription orders into the control system. The devices 28 then process the prescription orders to fill vials or other containers through a partially automated process for particular patients or customers. As discussed in U.S. patent application Ser. No. 12/870,045, each device 28 includes a gantry assembly that moves the pharmaceuticals within the device 28 for access by the user. Operation (e.g., movement) of the gantry assembly is controlled by the control system based on the inputted prescription orders.

After the vials and unit of use packs are filled, the filled vials and packs can be transferred directly to a pharmacist for sale to a customer or can be transferred to the will call area 18 for temporary storage until a customer arrives. For example, filled vials and packs are transferred to the will call area 18 when a customer is coming for next day pickup or at a later time. Conveyors 30 are positioned adjacent the devices 26 to hold the filled vials and packs until the vials and packs can be taken to the will call area 18 or the sales area 22. In some embodiments, the conveyors 30 may be automated and configured to automatically transfer the filled vials and packs to the will call area 18 and/or the sales area 22.

Existing will call systems process prescriptions under the assumption that the prescriptions are sold. That is, the existing systems remove the filled prescriptions from on-hand inventory and decrease a refill counter accordingly, no matter how long the filled prescription sits in will call. However, as much as 20% of filled will call orders are never claimed and must be returned to stock. In most states, unclaimed prescriptions typically must be reversed and insurance money must be refunded within ten days. Pharmacies, however, normally wait fourteen days before reversing transactions since it is very time consuming to go through and locate unclaimed prescription vials. Furthermore, pharmacies often may claim to be out of a particular drug, yet still have doses of the drug sitting unclaimed in will call.

In contrast to existing will call systems, the system 10 illustrated in FIGS. 1-3 places filled prescription vials and packs in a sales pending state. In this state, the total inventory of a particular pharmaceutical (regardless of whether that pharmaceutical is part of a filled prescription) remains visible in the system 10 until a customer actually comes to claim and pick up the filled prescription. Unclaimed pharmaceuticals can thereby be used to fill other prescriptions that are claimed beforehand.

The illustrated will call area 18 includes a storage tower or unit 34 for receiving and storing filled vials from the pharmaceutical storage and retrieval devices 28 in the production area 14. Overall, the storage unit 34 is similar to each of the devices 28, but is a simplified or stripped-down version of one of the devices 28 because the storage unit 34 does not need a user interface or inlet and outlet ports. The storage unit 34 is a high-density storage unit that is configured to hold and store over 1000 filled prescription vials at a time. In some embodiments, the storage unit 34 may be about ten feet long and may hold more than 6000 filled vials. In other embodiments, the size of the storage unit 34 may vary to hold fewer or more filled vials, depending on the need of the pharmacy.

As shown in FIG. 2, the storage unit 34 includes a storage space 35 and a gantry assembly 36. The storage space 35 is configured to receive and store the filled vials of pharmaceuticals. Shelves or other suitable structures may be positioned within the storage space 35 to facilitate storing the filled vials in an orderly manner. The gantry assembly 36 is movable within the storage space 35 to position and retrieve the vials. Similar to the gantry assembly disclosed in U.S. patent application Ser. No. 12/870,045, the illustrated gantry assembly 36 includes a gripper assembly 37 that can grasp the vials and is operated by a control system having a processor and memory.

Referring to FIG. 3, the illustrated storage unit 34 also includes a feeder 39 to help load filled vials into the unit 34. The feeder 39 allows a user to position a group of filled vials on the storage unit 34 without having to manually load the vials into particular locations within the storage space 35. Instead, the filled vials can be placed on the feeder 39 by the user, and the gantry assembly 36 can load the vials from the feeder 39 into the storage space 35. Such an arrangement allows the user to rapidly feed filled vials into the storage unit 34 without having to check and confirm the proper location for each vial with the storage space 35. As the gantry assembly 36 loads the vials into the storage space 35, the control system (which may be integrated with the control system of the devices 28) tracks the location of each of the vials in the storage unit 34. In the illustrated embodiment, the feeder 39 includes a horizontal shelf with a series of cubby holes, or ports, for temporarily receiving the vials. In other embodiments, the feeder 39 may include a vertical dispenser column or other suitable structure that receives the vials until the vials are loaded into the storage space 35 by the gantry assembly 36.

The storage unit 34 also includes an automatic scanner 40 (e.g., a bar code scanner, a RF scanner, etc.) and a scale 41. The scanner 40 identifies the vials as the vials move into and/or out of the unit 34. The scanner 40 thereby helps track the location of each vial within the storage space 35 as the gantry assembly 36 moves the vials. The scale 41 weighs the vials as the vials are loaded into the storage unit 34 to verify that the vial was properly filled. For example, the scanner 40 scans the vial to determine the type and amount of pharmaceuticals that are expected to be in the vial, and the scale 41 weighs the vial to determine the weight of the vial. The control system then compares the weight of the vial to an expected weight (based on information stored in a database) to determine whether the vial was properly filled. If properly filled, the vial is loaded into and stored in the storage unit, and the location of the vial is saved in memory. If improperly filled, a notification (e.g., a text message, email alert, alarm, audible message, displayed message, etc.) is delivered to the user. The user can then refill the vial properly and load the refilled vial onto the feeder 40. In some embodiments, the scanner 40 and the scale 41 can be integrated into the gripper assembly 37 of the gantry assembly 36 such that the scanning and weighing functions occur as the gantry assembly 26 moves and loads the vials. In other embodiments, such as the illustrated embodiment, the scanner 40 and the scale 41 may be located on the feeder 40.

The illustrated will call area 18 also includes a secondary storage machine 38 for receiving and storing containers that have different sizes and shapes than the vials. In particular, the containers are shaped and sized such that they are incompatible with (i.e., too large, bulky, or cumbersome for) the storage unit 34. The containers are filled "unit of use" packs such as, for example, inhalers, syringes, bandages, and other devices not suitable for storage in a prescription vial. The secondary storage machine 38 may include a rotating rubber belt with vanes to divide and move the filled packs to an exit port. An inlet port 43 in a top surface of the storage machine 38 allows a user to insert containers into the machine 38 between the vanes. In some embodiments, removable patient labels may be applied to the filled packs before the packs are placed in the secondary storage machine 38 to help identify the packs. Additionally or alternatively, the storage machine 38 may be refrigerated for storing certain types pharmaceuticals, such as insulin.

When a customer arrives to pick up his or her prescription, the filled prescription vials can be dispensed from the storage unit 34 through tubes 42 or other suitable conduits. The tubes 42 extend from an outlet of the storage unit 34 generally toward the sales area 22. The tubes 42 are configured to receive one or more vials from the gantry assembly 36 to direct the vials toward the customer. In the illustrated embodiment, each tube 42 includes a sensor 44 (e.g., an infrared or laser beam) that detects movement of the vials through the tube 42. The sensors 44 verify that a vial actually was dispensed out of the storage unit 34.

Similarly, the filled containers may be dispensed from the secondary storage machine 38 through tubes 46 or other suitable conduits. The tubes 46 extend from the exit port of the machine 38 generally toward the sales area 22. As the belt within the machine 38 rotates, a plunger or other suitable mechanism within the machine 38 pushes the containers through the exit port and into the tubes 46. In the illustrated embodiment, each tube 46 includes a sensor 48 (e.g., an infrared or laser beam) that detects movement of the containers through the tube 46. The sensors 48 verify that a container actually was dispensed out of the secondary storage machine 38.

The sales area 22 receives the filled vials and containers from the will call area 18. The illustrated sales area 22 includes two automated kiosks 50 and a counter 54. Depending on where a customer goes to pick up his or her prescription, the storage unit 34 and the secondary storage machine 38 may dispense the filled prescription to either one of the kiosks 50 or a pharmacist working at the counter 54.

The kiosks 50 include touch screens, signature capture systems, and credit/debit payment systems. In some embodiments, the kiosks 50 may require a customer to login using a username and/or password in order to use and operate the kiosks 50. The kiosks 50 also include a slidable bank drawer-type device and a printer. The drawer-type device receives the filled prescription from the tubes 42, 46 and releases the prescription to a customer once identification and payment are approved. The printer prints associated paperwork for the prescription, such as instructions for use and receipts. In some embodiments, the printer may not print the paperwork until requested by the customer. Such an arrangement reduces paper waste if the customer is already familiar with the prescription. Each kiosk 50 can also include a camera to monitor the customer as the customer interacts with the kiosk 50. Unlike the counter 54, the kiosks 50 allow a customer to pick up his or her prescription after hours when a pharmacist is no longer available.

Each kiosk 50 may also include a detector or sensor to detect that the customer actually takes the prescription and printed material from the kiosk 50. The kiosks 50 may also include a recovery feature to "pull back" filled vials and packs (as well as any associated printed material) if a customer walks away without taking his or her prescription. For example, if the customer does not open the lid of the drawer-type device within a certain period of time (e.g., one minute), the kiosk 50 can automatically slide back behind a wall of the pharmacy and drop the unclaimed prescription into a collection bin. This feature can help protect confidential patient healthcare information.

The filled vials and packs from the will call area 18 can alternatively be dropped into catch bins 58 behind a wall of the pharmacy. The bins 58 are accessible directly by the pharmacy staff. The bins 58 allow the vials and packs to be delivered to customers from a pharmacist, or other staff member, working at the counter 54 rather than through the kiosks 50.

The storage unit 34 and the secondary storage machine 38 allow storage of filled vials and packs without printing drug information and/or patient-specific information on, for example, a monograph. Such an arrangement reduces the amount of storage space needed for the monographs. Instead, the monograph can be printed when the customer arrives to pick up the vial or pack at one of the kiosks 50 or at the counter 54. A customer can also choose not to have this information printed if the customer is already familiar with the prescription, reducing excess paper waste.

The storage unit 34 and the secondary storage machine 38 can also automatically return filled vials and containers to the pharmaceutical storage and retrieval devices 28 if the vials or containers are unclaimed by a customer after a predetermined period of time. Once a prescription order is filled, the filled vials or containers are loaded into the storage unit 34 or the storage machine 38, as described above. The control system monitors a length of time that the vials and containers are stored in the unit 34 or the machine 38. Alternatively, the control system can monitor a length of time from when the prescriptions are filled. If the filled vials and containers are unclaimed after, for example, ten days, the storage unit 34 and the secondary storage machine 38 direct the unclaimed vials and containers to a tote or bin (e.g., one of the bins 58) behind a wall of the pharmacy for restocking in the devices 28. The gantry assembly 36 in the storage unit 34 and the plunger in the secondary storage machine 38 are operated by the control system to direct the unclaimed vials and containers into a suitable bin using one of the corresponding conduits 42, 46. This automatic unloading may occur overnight while the pharmacy is closed and not in operation.

In the morning, pharmacy staff collects the unclaimed vials and containers from the bin. The staff then transfers the vials and containers back to the pharmaceutical storage and retrieval devices 28 in the production area 14 by inserting the filled vials and containers into inlet ports in the devices 28. The unclaimed, filled vials and containers are thereby placed back into stock. The filled vials and containers are returned to the devices 28 without removing the pharmaceuticals stored inside the vials and containers. In some scenarios, patient labels may also be left on the vials because the devices 28 are enclosed and, thereby, prevent users or other personnel from reading or accessing the pharmaceuticals stored in the devices 28. That is, the labels do not need to be altered (e.g., blacked-out, removed, or otherwise obliterated) when the vials are returned to the devices 28. In such scenarios, the vials may be re-dispensed if the appropriate customer ever arrives to claim the vials. Alternatively, the patient labels may be removed once the vials are needed to fill a prescription order for a different customer.

The system 10 requires fewer technicians to fill orders, maintains accurate inventory in a secure manner, allows visibility of finished (e.g., filled) vial and pack inventory, and stores the finished inventory securely. The system 10 thereby provides, among other things, higher security, accuracy in delivering the correct items to patients, a single location for storage of all finished/filled goods, and a kiosk delivery system for self-checkout.

Various features and advantages of the invention are set forth in the following claims.

The invention claimed is:

1. A method of filling prescription orders, the method comprising:
inputting the prescription orders into a pharmaceutical storage and retrieval device;
processing the prescription orders with the pharmaceutical storage and retrieval device to fill a plurality of vials with desired pharmaceuticals;
transferring the plurality of filled vials from the pharmaceutical storage and retrieval device to a storage unit;
storing the plurality of filled vials in the storage unit until a customer claims one of the plurality of filled vials; and
directing the one of the plurality of filled vials from the storage unit to a store kiosk that is accessible to the customer,
wherein a conduit extends from an outlet of the storage unit to the store kiosk, and wherein directing the one of the plurality of filled vials includes directing the one of the plurality of filled vials through the conduit from the storage unit to the store kiosk,
wherein transferring the plurality of filled vials includes moving the plurality of filled vials from the pharmaceutical storage and retrieval device to a feeder of the storage unit, and
wherein the storage unit includes a gantry assembly, and further comprising operating the gantry assembly to move the plurality of filled vials from the feeder to a storage space inside the storage unit.

2. The method of claim 1, further comprising operating the gantry assembly to retrieve the one of the plurality of filled vials from the storage space of the storage unit when the customer claims the one of the plurality of filled vials.

3. The method of claim 1, wherein the storage unit is a high-density storage unit, and wherein storing the plurality of filled vials includes simultaneously storing over one thousand filled vials in the storage unit.

4. The method of claim 1, further comprising verifying, at the storage unit, that each of the plurality of filled vials is correctly filled.

5. The method of claim 4, wherein the storage unit includes at least one of a bar code scanner and a scale, and wherein verifying that each of the plurality of filled vials is correctly filled includes at least one of scanning each of the plurality of filled vials with the bar code scanner and weighing each of the plurality of filled vials with the scale.

6. The method of claim 1, further comprising:
storing a plurality of filled containers in a secondary storage machine until the customer claims one of the plurality of filled containers, the plurality of filled containers having different sizes and shapes than the plurality of filled vials; and
directing the one of the plurality of filled containers from the secondary storage machine to the customer.

7. The method of claim 6, wherein directing the one of the plurality of filled vials includes directing the one of the plurality of filled vials from the storage unit through a first conduit to the customer, and wherein directing the one of the plurality of containers includes directing the one of the plurality of containers from the secondary storage machine through a second conduit to the customer.

8. The method of claim 6, further comprising refrigerating the plurality of containers stored within the secondary storage machine.

9. A method of filling prescription orders, the method comprising:
inputting the prescription orders into a pharmaceutical storage and retrieval device;
processing the prescription orders with the pharmaceutical storage and retrieval device to fill a plurality of vials with desired pharmaceuticals;
transferring the plurality of filled vials from the pharmaceutical storage and retrieval device to a storage unit;
storing the plurality of filled vials in the storage unit until a customer claims one of the plurality of filled vials;
directing the one of the plurality of filled vials from the storage unit to a store kiosk that is accessible to the customer;
wherein a conduit extends from an outlet of the storage unit to the store kiosk, and wherein directing the one of the plurality of filled vials includes directing the one of the plurality of filled vials through the conduit from the storage unit to the store kiosk; and
detecting, by a sensor coupled to the conduit, movement of the one of the plurality of filled vials through the conduit.

10. A method of restocking unclaimed prescription orders, the method comprising:
filling a vial with pharmaceuticals using a pharmaceutical storage and retrieval device;
transferring the filled vial from the pharmaceutical storage and retrieval device to a storage space of a storage unit;
storing the filled vial in the storage unit until a customer claims the filled vial;
monitoring a length of time that the filled vial is stored in the storage unit;
directing the filled vial out of the storage space and into a bin of the storage unit when the filled vial is unclaimed by the customer after a predetermined period of time; and
returning the filled vial from the bin to the pharmaceutical storage and retrieval device.

11. The method of claim 10, wherein returning the filled vial includes returning the filled vial to the pharmaceutical storage and retrieval device if the filled vial is unclaimed by the customer after ten days.

12. The method of claim 10, wherein returning the filled vial to the pharmaceutical storage and retrieval device includes collecting the filled vial from the bin and inserting the filled vial into the pharmaceutical storage and retrieval device.

13. The method of claim 10, wherein the storage unit includes a gantry assembly, and further comprising operating the gantry assembly to move the filled vial from the storage unit to the bin.

14. The method of claim 10, further comprising storing the returned vial within the pharmaceutical storage and retrieval device without removing the pharmaceuticals from the returned vial.

15. The method of claim 14, wherein storing the returned vial includes storing the returned vial within the pharmaceutical storage and retrieval device without altering a label on the returned vial.

* * * * *